(12) United States Patent
Burtscher et al.

(10) Patent No.: US 6,475,764 B1
(45) Date of Patent: Nov. 5, 2002

(54) RECOMBINANT COLLAGENASE TYPE I FROM CLOSTRIDIUM HISTOLYTICUM AND ITS USE FOR ISOLATING CELLS AND GROUPS OF CELLS

(75) Inventors: Helmut Burtscher, Habach; Dorothee Ambrosius; Friederike Hesse, both of Munich, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/308,453

(22) PCT Filed: Oct. 30, 1997

(86) PCT No.: PCT/EP97/06002

§ 371 (c)(1),
(2), (4) Date: Sep. 9, 1999

(87) PCT Pub. No.: WO98/22574

PCT Pub. Date: May 28, 1998

(30) Foreign Application Priority Data

Nov. 19, 1996 (EP) .......................... 96 118 490
Jan. 24, 1997 (EP) .......................... 97 101 085

(51) Int. Cl.⁷ .......................... C12N 9/52; C12N 15/52; C12N 15/57; C12N 15/74; C07G 17/00

(52) U.S. Cl. .................. 435/220; 435/69.1; 435/252.3; 435/320.1; 435/267

(58) Field of Search .......................... 435/220, 267

(56) References Cited

U.S. PATENT DOCUMENTS

| | | | |
|---|---|---|---|
| 5,177,011 A | 1/1993 | Shewmaker et al. | 435/172.3 |
| 5,177,017 A | 1/1993 | Lin et al. | 435/252.33 |
| 5,418,157 A | 5/1995 | Lin et al. | 435/220 |
| 5,763,257 A * | 6/1998 | Bott et al. | 435/221 |

FOREIGN PATENT DOCUMENTS

| | | | |
|---|---|---|---|
| EP | 0 677 586 A1 | 10/1995 | ............ C12N/15/57 |
| WO | WO 91/14447 | 10/1991 | ............ A61K/37/54 |
| WO | WO 94/00580 | 1/1994 | ............ C12N/15/57 |

OTHER PUBLICATIONS

Matsushita et al., 1999, "Gene duplication and multiplicity of collagenases in Clostridium histolyticum", Journal of Bacteriology, vol. 181, pp. 923–933.*

Eddie L. Angleton, et al., "Preparation and Reconstitution with Divalent Metal Ions of Class I and Class II Clostridium histolyticum Apocollagenases" Biochemistry 27:7406–7412 (1988).

Eddie L. Angleton, et al., "Preparation by Direct Metal Exchange and Kinetic Study of Active Site Metal Substituted Class I and Class II Clostridium histolyticum Collagenases," Biochemistry 27:7413–7418 (1988).

Michael D. Bond, et al., "Purification and Separation of Individual Collagenases of Clostridium histolyticum Using Red Dye Ligand Chromatography," Biochemistry 23:3077–3085 (1984).

Michael D. Bond, et al., "Characterization of the Individual Collagenases from Clostridium histolyticum," Biochemistry 23:3085–3091 (1984).

Mark F. French, et al., "Identification of Clostridium histolyticum Collagenase Hyperreactive Sites in Type I, II and III Collagens: Lack of Correlation with Local Triple Helical Stability," Journal of Protein Chemistry 11:83–97 (1992).

(List continued on next page.)

Primary Examiner—Tekchand Saidha
Assistant Examiner—William W. Moore
(74) Attorney, Agent, or Firm—Kenneth J. Waite; Roche Diagnostics Corporation (57) ABSTRACT

A polypeptide with the properties of collagenase class I from Clostridium histolyticum (CHC I) and the amino acid sequence SEQ ID NO:2 which is optionally N-terminally extended by one or several amino acids of the sequence SEQ ID NO:3 is advantageously suitable for the isolation of cells from mammalian tissue and human tissue.

6 Claims, 1 Drawing Sheet

OTHER PUBLICATIONS

Thomas J. Hefley, "Utilization of FPLC–Purified Bacterial Collagenase for the Isolation of Cells from Bone," Journal of Bone and Mineral Research 2:505–516 (1987).

C. Holzinger, et al., "Effects of interleukin–1, –2, –4, –6, interferon–gamma and granulocyte/macrophage colony stimulating factor on human vascular endothelial cells," Immunology Letters 35–109–118 (1993).

J. R. Quibel, et al., "Use of Specific Collagenases for the Isolation of Rat Liver Cells with Preserved Lipase Activities," Analytical Biochemistry 154:26–28 (1986).

Marina Schorpp, et al., "Structural organization and chromosomal localization of the mouse collagenase type I gene," Biochem J 308:211–217 (1995).

Smyth Templeton, et al., "Cloning and Characterization of Human Tumor Cell Interstitial Collagenase," Cancer Research 50:5431–5437 (1990).

Robert Sutton, et al., "Isolation of Rat Pancreatic Islets by Ductal Injection of Collagenase," Brief Communications 42:689–691 (1986).

Harold E. Van Wart, et al., "Complementary Substrate Specificities of Class I and Class I Collagenases from Clostridium histolyticum," Biochemistry 24:6520–6526 (1985).

* cited by examiner

Fig. 1

RECOMBINANT COLLAGENASE TYPE I FROM CLOSTRIDIUM HISTOLYTICUM AND ITS USE FOR ISOLATING CELLS AND GROUPS OF CELLS

The present invention claims priority to the following applications: 1) EP 96 118 490.0, filed Nov. 19, 1996; 2) EP 97 101 085.5, filed Jan. 24, 1997; and 3) PCT/EP97/06002, filed Oct. 30, 1997.

The invention concerns a recombinant collagenase type I (CHC I) from Clostridium histolyticum and its use for isolating cells and groups of cells.

Bacterial collagenases, e.g. from Clostridium histolyticum, are used to digest tissues and to isolate individual cells or groups of cells (e.g. islets) (islets: Sutton et al., Transplantation 42 (1986) 689–691; liver: Quibel et al., Anal. Biochem. 154 (1986) 26–28; bones: Hefley et al., J. Bone Mineral Res. 2 (1987) 505–516; umbilical cord: Holzinger et al., Immunol. Lett. 35 (1993) 109–118). Two different collagenase types are known from Clostridium histolyticum (M. F. French et al., J. Protein Chemistry 11 (1992) 83–97). The isolation and purification of collagenases from Clostridium histolyticum is described for example in E. L. Angleton and H. E. van Wart, Biochemistry 27 (1988) 7413–7418 and 7406–7412.

Collagenases I were isolated and described by M. D. Bond and H. E. Van Wart, Biochemistry 23 (1984) 3077–3085 and 3085–3091 as well as by H. E. Van Wart, Biochemistry 24 (1985) 6520–6526. Accordingly the collagenases a (MW 68 kD), β (MW 115 kD), γ (MW 79 kD) and η (MW 130 kD) are known as collagenases I. Collagenases I and collagenases II differ in their relative activity towards collagen and towards synthetic peptides. Collagenases I have higher activities towards collagen and gelatin and lower activities towards the short-chained peptides than collagenase II (Bond and Wart, Biochemistry 23 (1984) 3085–3091).

Further collagenases are described in the U.S. Pat. Nos. 5,418,157 and 5,177,011 with a molecular weight of 68 kD. WO 91/14447 also describes a collagenase with a molecular weight of 68 kD. A recombinant collagenase with a molecular weight of ca. 110 kD is described in WO 94/00580 and a sequence is stated for it. Nothing is stated in WO 94/00580 about its specificity and in particular whether it is a collagenase I or II. In addition to a collagenase with a molecular weight of 110 kD, a 125 kD collagenase is additionally mentioned which it is claimed can also be produced recombinantly. However, WO 94/00580 does not give more details about this collagenase.

The object of the present invention is to provide a highly active stable collagenase class I from Clostridium histolyticum (CHC I).

The object is achieved by a process for the production of a polypeptide which has the properties of a CHC I from Clostridium histolyticum, has a given amino acid composition and is obtainable by expression of an exogenous nucleic acid in prokaryotic or eukaryotic host cells and isolation of the desired polypeptide wherein the nucleic acid codes for a polypeptide having sequence ID NO:2 or a polypeptide which is extended N-terminally by one or several amino acids having the sequence ID NO:3.

It has surprisingly turned out that a CHC I according to the invention has a high collagenase class I activity and is very stable. A CHC I having the amino acid sequence SEQ ID NO:2 and a CHC I which is N-terminally extended by one or several amino acids having SEQ ID NO:3 are particularly preferred.

The CHC I according to the invention is a highly pure enzyme which can be produced in large amounts. The CHC I according to the invention is not contaminated by other clostridial enzymes and is free of toxins.

The CHC I according to the invention is especially suitable for isolating cells from tissues of mammals, preferably from human tissue, for an application in cell therapy (transplantation, immunotherapy) and for an application in gene therapy in tissues: e.g. pancreas, liver, bone, cartilage, skin, brain and nerve tissue, fat, muscle, heart, endothelium, kidney, solid tumours and for the purification of ulcers.

In addition this highly pure enzyme (preferably in a mixture with other-highly pure enzymes (such as collagenase II and neutral protease)) is particularly suitable for the isolation of cells whose surface molecules/markers (antigens) should not be changed. Preferred applications of this are for example the dissociation of solid tumours of all types in vitro (e.g. colon, breast etc.) for adoptive immunotherapy and for general diagnosis such as e.g. to detect rare cells. from tissues and solid tumours by means of specific surface markers/molecules.

The production of the recombinant CHC I can be carried out according to methods familiar to a person skilled in the art.

For this a DNA molecule is firstly produced which is capable of producing a protein which has the activity of CHC I. The DNA sequence is cloned into a vector which can be transferred into a host cell and can be replicated there. Such a vector contains promoter/operator elements which are necessary to express the DNA sequences in addition to the CHC I sequence. This vector which contains the CHC I sequence and the promoter/operator elements is transferred into a host cell which is able to express the DNA of CHC I. The host cell is cultured under conditions which are suitable for the amplification of the vector and CHC I is isolated. In this process suitable measures ensure that the protein can adopt an active tertiary structure in which it exhibits CHC I properties.

The nucleic acid sequence and protein sequence can be modified to the usual extent. Such modifications are for example:

Modification of the nucleic acid in order to introduce various recognition sequences of restriction enzymes to facilitate the steps of ligation, cloning and mutagenesis.

Modification of the nucleic acid to incorporate preferred codons for the host cell.

Extension of the nucleic acid by additional operator elements in order to optimize the expression in the host cell.

Substitution or deletion of amino acids while retaining the basicity and the spatial structure of CHC I. It is advantageous to preserve 85% or more and preferably 90% or more of the original amino acid sequence.

A further subject matter of the invention is a polypeptide with the properties of a collagenase class I from Clostridium histolyticum with the amino acid sequence according to SEQ ID NO:2 or a polypeptide extended N-terminally by one or several amino acids of SEQ ID NO:3. A further subject matter of the invention is a nucleic acid coding for such a protein.

The protein is preferably produced recombinantly in microorganisms, in particular in prokaryotes and in this case in *E. coli*.

Suitable expression vectors must contain a promoter which allows expression of the protein in the host organism. Such promoters are known to a person skilled in the art and are for example the lac promoter (Chang et al., Nature 198

(1977) 1056), trp promoter (Goeddel et al., Nuc. Acids Res. 8 (1980) 4057), $\lambda_{PL}$ promoter (Shimatake et al., Nature 292 (1981) 128) and T5 promoter (U.S. Pat. No. 4,689,406). Synthetic promoters are also suitable such as for example the tac promoter (U.S. Pat. No. 4,551,433). Coupled promoter systems are also suitable such as the T7-RNA polymerase/promoter system (Studier et al., J. Mol. Biol. 189 (1986) 113). Hybrid promoters composed of a bacteriophage promoter and the operator region of the microorganism (EP-A 0 267 851) are equally suitable. An effective ribosome binding site is necessary in addition to the promoter. In the case of E. coli this ribosome binding site is denoted the Shine-Dalgarno (SD) sequence (Sambrook et al., "Expression of cloned genes in E. coli" in Molecular Cloning: A laboratory manual (1989) Cold Spring Harbor Laboratory Press, New York, USA).

In order to improve the expression it is possible to express the protein as a fusion protein. In this case a DNA sequence which codes for the N-terminal part of an endogenous bacterial protein or for another stable protein is usually fused to the 5' end of the DNA coding for the CHC I. Examples of this are for example lacZ (Phillips and Silhavy, Nature 344 (1990) 882–884), trpE (Yansura, Meth. Enzymol. 185 (1990) 161–166).

After expression of the vector, preferably a biologically functional plasmid or a viral vector, the fusion proteins are preferably cleaved with enzymes (e.g. factor Xa) (Nagai et al., Nature 309 (1984) 810). Other examples of cleavage sites are the IgA protease cleavage site (WO 91/11520, EP-A 0 495 398) and the ubiquitin cleavage site (Miller et al., Bio/Technology 7 (1989) 698).

The proteins expressed in this manner in bacteria are isolated in the usual way by lysing the bacteria and protein isolation.

In a further embodiment it is possible to secrete the proteins as active proteins from the microorganisms. For this a fusion product is preferably used which is composed of a signal sequence which is suitable for the secretion of proteins in the host organisms used and the nucleic acid which codes for the protein. In this process the protein is either secreted into the medium (in the case of gram-positive bacteria) or into the periplasmic space (in the case of gram-negative bacteria). It is expedient to place a cleavage site between the signal sequence and the sequence coding for CHC I which enables cleavage of the protein either during processing or in an additional step. Such signal sequences are derived for example from ompA (Ghrayeb et al. EMBO J. 3 (1984) 2437) or phoA (Oka et al., Proc. Natl. Acad. Sci. USA 82 (1985) 7212).

The vectors in addition also contain terminators. Terminators are DNA sequences which signal the end of a transcription process. They are usually characterized by two structural features: an inverse repetitive G/C-rich region which can intramolecularly form a double helix and a number of U(or T) residues. Examples are the main terminator in the DNA of the phage fd (Beck and Zink, Gene 16 (1981) 35–58) and rrnB (Brosius et al., J. Mol. Biol. 148 (1981) 107–127).

In addition the expression vectors usually contain a selectable marker in order to select the transformed cells. Such selectable markers are for example the resistance genes for ampicillin, chloroamphenicol, erythromycin, kanamycin, neomycin and tetracyclin (Davies et al., Ann. Rev. Microbiol. 32 (1978) 469). Selectable markers which are also suitable are the genes for substances that are essential for the biosynthesis of substances necessary for the cell such as e.g. histidine, tryptophan and leucine.

Numerous suitable bacterial vectors are known. Vectors have for example been described for the following bacteria: Bacillus subtilis (Palva et al., Proc. Natl. Acad. Sci. USA 79 (1982) 5582), E. coli (Aman et al., Gene 40 (1985) 183; Studier et al., J. Mol. Biol. 189 (1986) 113), Streptococcus cremoris (Powell et al., Appl. Environ. Microbiol. 54 (1988) 655), Streptococcus lividans and Streptomyces lividans (U.S. Pat. No. 4,747,056).

Further genetic engineering methods for the construction and expression of suitable vectors are described in J. Sambrook et al., Molecular Cloning: A laboratory manual (1989), Cold Spring Harbor Laboratory Press, New York, N.Y.

Apart from in prokaryotic microorganisms, recombinant CHC I can also be expressed in eukaryotes (such as for example CHO cells, yeast or insect cells). The yeast system or insect cells is preferred as the eukaryotic expression system. Expression in yeast can be achieved by means of three types of yeast vectors (integrating YIp (yeast integrating plasmids) vectors, replicating YRp (yeast replicon plasmids) vectors and episomal YEp (yeast episomal plasmids) vectors. More details of this are for example described in S. M. Kingsman et al., Tibtech 5 (1987) 53–57).

The invention in addition concerns a process for disintegrating cell tissue and releasing cells or groups of cells contained therein by incubating the cell tissue with a collagenase class I from Clostridium histolyticum until the cells or groups of cells have been released to the desired extent and separating the cells or groups of cells from the cell tissue fractions. The separation of the cells or groups of cells from the cell tissue fractions is preferably carried out by centrifugation using a density gradient.

Cells or groups of cells are usually isolated from tissues (e.g. pancreas, liver, skin, endothelium, umbilical cord, bone, tumour tissue) by incubating organs, parts of organs or tissues with enzymes which dissolve the surrounding extracellular connective tissue matrix (islets: Sutton et al., Transplantation 42 (1986) 689–691; liver: Quibel et al., Anal. Biochem. 154 (1986) 26–28; bone: Hefley et al., J. Bone Mineral Res. 2 (1987) 505–516); umbilical cord: Holzinger et al., Immunol. Lett. 35 (1993) 109–118). Tumour cells isolated in this manner can be used advantageously for tumour vaccination and/or adoptive immunotherapy. Tissue disintegration can also be carried out by perfusing the entire organ (Ricordi et al., Diabetes 37 (1988) 413–420) with an enzyme solution. Important factors in this process, in addition to the composition of the enzyme mixture, are the duration, the pH value and the temperature of the digestion as well as the mechanical action e.g. by shaking and addition of metal balls. Since extracellular connective tissue matrix often has a high proportion of collagen, collagenases play a special role (Wolters, Hormone and Metabolic Research 26 (1994), 80).

The process according to the invention is preferably used to isolate islets or islet cells from pancreatic tissue.

In addition, the addition of further enzymes such as proteinases (e.g. neutral protease, cf. example 5 or other metalloproteases; serine proteases such as trpysin, chymotrypsin, plasmin etc.; cysteine proteases; aspartate proteases), elastases, hyaluronidase, lipases or other collagenases may be advantageous for the quality of the digestion.

The invention is further elucidated by the following examples, the figure and the sequence protocol.

The sequence protocols denote:

SEQ ID NO: 1: DNA fragment of CHC I

SEQ ID NO: 2: derived protein fragment

SEQ ID NO: 3: N-terminal extension
SEQ ID NO: 4: 4–24: primers and peptide fragments

EXAMPLE 1

Purification of the Collagenase Class I (CHC I)

1 g collagenase P (from Clostridium histolyticum, Boehringer Mannheim GmbH, cat. No. 1 213 857) was dissolved in 20 ml $H_2O$ (milli Q quality) and particulate components were removed by centrifugation. After a 60% ammonium sulfate precipitation, the precipitate was taken up in 9.5 ml $H_2O$ and dialysed overnight at 4° C. against 10 mM Tris-HCl, pH 7.5.

The dialysate was applied at room temperature to a Zn-chelate Sepharose column (column volume CV=50 ml, 2 cm diameter). Subsequently the column was washed with 10 mM Tris HCl, pH 7.5.

The eluant peak which contains the CHC I fractions was further separated on a Mono Q column (Pharmacia) in 10 mM/l Tris HCl, pH 7.5 using a linear gradient up to 10 mM/l Tris, pH 7.5, 0.3 M/l NaCl. The peak containing the CHC I activity (activity determined as azocoll activity according to Chavira et al., Anal. Biochem. 136 (1984) 446–450) is further purified by means of reversed phase HPLC (mobile solvent A: 0.12% TFA (trifluoroacetic acid/$H_2O$, 25% acetonitrile, step gradient up to 50% acetonitrile within 5 min and up to 70% acetonitrile within 15 min). The fraction of the second gradient stage containing the main peak is evaporated to dryness and, after carboxymethylation, subjected to digestion with endoproteinase LysC. The peptides were also separated by reversed phase HPLC (Vydac C4) with a gradient of 5–45% acetonitrile/0.12% TFA within 105 min. The peptides were collected, evaporated to dryness and sequenced.

EXAMPLE 2

Cloning of the Collagenase Class I from Clostridium Histolyticum 2.1 A 1.4 kB segment of the CHC I gene that was derived from peptide sequences that had been obtained by digestion of purified collagenase I from Clostridium histolyticum according to example 1 was isolated with the aid of a PCR reaction. This segment or fragments thereof were used to prepare a DNA probe which can for example be labelled with Dig. Such a probe is used to screen gene banks in order to isolate the remainder of the CHC I gene.
Peptide Sequences:
 Coll-I-2Q: F N S P E E Y (SEQ ID NO:4)
 Coll-I-72: E D G D V T I (SEQ ID NO:5)
Primers derived therefrom:
 Coll-1-2QF: 5' tty aay wsn ccn gar gar tay (SEQ ID NO:6)
 Coll-1-2QR: 5' rta ytc ytc ngg nsw rtt raa (SEQ ID NO:7)
 Coll-1-72F: 5' gar gay ggn gay gtn acn att (SEQ ID NO:8)
 Coll-1-72R: 5' dat ngt nac rtc ncc rtc ytc (SEQ ID NO:9)
Four primers were designed and used in two different PCR reactions (primer combinations 2QF/72R and 2QR/72F). Only the combination 2QF with 72R yielded a PCR product (length 1.4 kB) which corresponded to the sequence from position 2418 to 3806 of the total sequence shown in SEQ ID NO:1.

The identity of this piece and the reading frame on it were confirmed by recovery of additional peptide sequences of collagenase I from Clostridium histolyticum:

peptide 1-23: DWDEMSK (SEQ ID NO:10)
peptide 1-33: VTGPSTGAVGRNIEFSGK (SEQ ID NO:11)
peptide 1-40: NTEYQNHIQELVDK (SEQ ID NO:12)

Cloning of the Collagenase Class I from Clostridium Histolyticum

It was possible to isolate a DNA fragment of 5.4 kB in length which contained the entire 1.4 kB probe from a gene bank which was prepared from Stu I/HindII cleaved genomic DNA of Clostridium histolyticum with the aid of a digoxigenin-labelled fragment (derived from the above 1.4 kB fragment). DNA sequencing from the ends of the known 1.4 kB sequence enabled the CHC I sequence to be completed at the 3' end and extended at the 5' end up to a Stu I cleavage site.

The sequence at the 3' end corresponds to position 3807 to 4358 of the total sequence shown in SEQ ID NO:1.

The sequence of a further peptide of the wild-type enzyme was found in this sequence section:

peptide 1-67: EDGDVTIELPYSGSSNFTWLVY (SEQ ID NO:13)

A large part of this peptide overlaps with peptide 1–72 (SEQ ID NO:5) but it contains 4 additional amino acids which cannot yet be found on the original 1.4 kB DNA fragment.

The sequence at the 5' end corresponds to position 1969 to 2417 of the total sequence shown. in SEQ ID NO:1.

It was also possible to identify a DNA fragment of 4.6 kB from a Bgl II gene bank using the labelled 1.4 kB probe. This fragment proved to be not clonable as a whole but it was possible to sequence it from the Stu I site onwards and yielded further sequence information about the 5' region.

The sequence found corresponds to position 1630 to 1974 of the total sequence shown in SEQ ID NO:1.

It was possible to confirm that this sequence belongs to the collagenase I gene by discovery of a further peptide:

Peptide 1-42: QFRENLNQYAPDYVK (SEQ ID NO:14)
2.3 Inverse PCR

In an experiment aimed at gaining information about the 5' region of the gene by means of an inverse PCR, genomic DNA from Clostridium histolyticum cleaved with StuI was separated in an agarose gel, the 1.9–2.7 kB region was isolated (cut out of the gel), religated and amplified by inverse PCR:
Primers used:
 449-coll1: 5'-aga caa tgc ctt ggt atg g (SEQ ID NO:15)
 453-coll1-R: 5'-gtg aaa gtt tct ata ccc ttc (SEQ ID NO:16).

A fragment of 1.85 kB was obtained which could not be cloned as a whole but it was possible to determine a partial sequence.

This is position 1384 to position 1570 of the total sequence shown in SEQ ID NO:1.

This sequence is in the start region and immediately upstream of the previously described sequence for the collagenase I gene from Clostridium histolyticum.

2.4 Cloning of the 5' Region of the Collagenase I Gene from Clostridium Histolyticum Genomic DNA from Clostridium histolyticum was digested with HindIII/StuI and separated in an agarose gel. The region between 1.7 and 2.2 kB was cut out (expected fragment in Southern blot is at 1.9 kB). The DNA was isolated from the gel by conventional methods (QiaEx) and cloned into pUC19 by means of HindIII/HindII.

2.5 Gene Bank Screening

The HindIII/StuI gene bank was screened with a ca. 400 bp long Dig-labelled probe. The sequence of the probe corresponds to position 1453 to 1852 of the total sequence shown in SEQ ID NO:1.

The probe was prepared with the aid of two primers:

464-coll1: 5'-gta cag gtt ctc aaa agt tc (SEQ ID NO:17)

448-coll1-R:5'-gtt cct tta acg taa tca gg (SEQ ID NO:18)

Among ca. 2200 screened clones, there were 14 with a positive signal, plasmid minipreps were carried out on these using conventional methods, the best 4 clones all contained the same insert which corresponds to position 1–1971 of the total sequence shown in SEQ ID NO:1.

A total length for the CHC I gene and its upstream region of ca. 4.4 kB results with this sequence. The complete sequence is shown in SEQ ID NO:1.

A large open reading frame is positioned on this sequence which in the 3' region runs into the already described part of the collagenase I. Potential starting points for translation are located at position 1002 (ATG), 1029 (ATG), 1110 (ATG) as well as 1176 (GTG) and 1254 (GTG).

2.6 Constructs Extended in the 5' Region

An N-terminus of a possible mature form of the collagenase (IANTNSEK - SEQ ID NO:19) determined by protein sequencing is at position 1332 of SEQ ID NO:1. The corresponding polypeptide is shown in SEQ ID NO:2. Since all the translation starting points described above are further in the 5' direction and lie within the frame, several expression constructs were prepared and their expression properties were examined. It surprisingly turned out that starts at several positions each led to actively expressed enzymes. Examples of such constructs:

A SmaI or AvaI cleavage site can be introduced 5' before ATG 1002, 1029, 1110 or GTG 1176 or 1254 by suitable selection of the primers. If a counter primer is used which is located on the far side of the BfrI cleavage site (1965–1970), then all others can be prepared from a pUCBM20 expression vector by exchange via SmaI or AvaI and BfrI cleavage.

start at 1002: MTMITNSRA MKKNILKIL . . . (SEQ ID NO:20)

start at 1029: MTMITNSRA MDSYSKESK . . . (SEQ ID NO:21)

start at 1176: MTMITNSRA MKNIEEAKV . . . (SEQ ID NO:22) The underlined sequence is in each case a fusion part from pUCBM20 resulting from the construction.

It is known that GTG sequences may also come into consideration as a start position. A particularly preferred start is at GTG 1176 which can be converted into an ATG by selection of a suitable primer:

primer 472-Col1: 5'-ttc cca att gcc cgg gct atg aaa aat ata gaa gag gca aag (SEQ ID NO:23)

Figure 1:
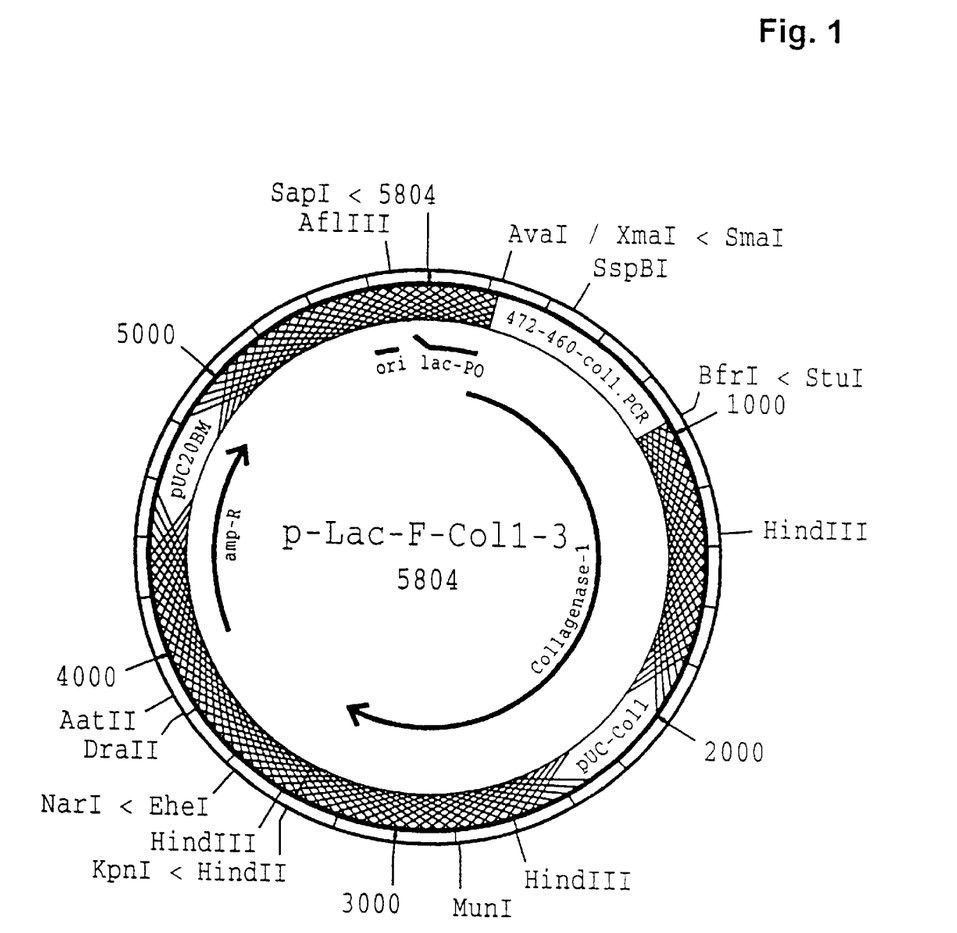
FIG. 1 shows the expression vector p-Lac-F-Col1-3.

This leads to the expression vector placF-col1-3 (FIG. 1).

2.7 Further Expression Possibilities

The expression constructs described previously use the lac promoter and the homologous signal peptide. Other promoters can be used equally well instead of these such as mgl (EP-B 0 285 152) or tac (EP-B 0 067 540).

The signal peptide can also be replaced by others e.g. the mgl signal peptide. Such a heterologous signal peptide should preferably be inserted directly in front of the mature 5' end of the collagenase gene. However, also in this case it turned out that several positions are conceivable. Hence an mgl signal in front of the peptide sequence IANTNSEK (SE ID NO:19) and in front of AYLTMNTS (SEQ ID NO:24) leads to active expression of CHC I. The fusion part from pUCBM20 caused by the construction is also not necessary. Expression still takes place when the fusion part is shortened or entirely removed. It is also possible to completely remove the signal and cytoplasmically express CHC I.

2.8 Strains

Known *E. coli* K12 strains such as e.g. C600, HB101 and similar ones are preferably used to express CHC I. Other prokaryotic systems and also gram-positive (e.g. bacillus or streptomyces) and expression in eukaryotic cell systems is also conceivable.

2.9 Molecular Weight purified (wild-type): ca. 115 kDa (after SDS gel electrophoresis)

purified (rec): ca. 115 kDa (after SDS gel electrophoresis)

theoret. (IANTNSEK): 113897 theoret. (AYLTMNTSS): 122547

EXAMPLE 3

Expression of Collagenase Class I 10 1 fermentation of the *E. coli* expression clone for CHC I and high pressure lysis Precultures are prepared from type cultures (plate smear, ampoules or paillettes) which are incubated at 30–37° C. while shaking.

The inoculation volume into the next higher dimension is 1–10 vol % in each case. Ampicillin (50–100 mg/l) is added to the preculture and main culture to select against plasmid loss.

Enzymatically digested protein and/or yeast extract as an N- and C-source as well as glycerol and/or glucose as an additional C-source can be used as nutrients. The medium is buffered to pH 7 and metal salts can be added at physiologically tolerated concentrations to stabilize the fermentation process.

The fermentation is carried out as a fed batch with a mixed protein/yeast extract dosage. The growth rate is regulated by the dosage rate and the pH value is controlled by means of glycerol and/or glucose as an acid regulator. The dissolved oxygen partial pressure ($pO_2$) is maintained at >20% in order to avoid anaerobic conditions by means of the aeration rate, rpm regulation and dosage rate. The fermentation temperature is 25–37° C.

The growth is determined by measuring the optical density at 528 nm. Expression of CHC I is induced by means of IPTG or lactose. After a fermentation period of ca. 30–40 h the biomass is harvested at OD standstill by centrifugation.

The biomass is taken up in a suitable buffer and lysed by a continuous high pressure press at 1000 bar. The suspension obtained in this manner is again centrifuged and the supernatant which contains dissolved CHC I is processed further.

EXAMPLE 4

Islet Isolation from Porcine Pancreas

The pancreas is prepared from a freshly slaughtered pig and cooled in ice-cold HBSS buffer (Gibco) until further processing. A cannula is inserted into the ductus pancreaticus and fastened there, the water-tightness of the pancreas is tested using HBSS buffer. An enzyme solution in HBSS buffer+$Ca^{2+}$which contains purified recombinant collagenase type I alone or in combination with a purified native or recombinant neutral protease and/or collagenase type II from Clostridium histolyticum is injected. The pancreas treated in this way is connected to the perfusion unit that also contains the above-mentioned enzyme solution (discontinuous perfusion). The digestion is carried out between 4° C. and 37° C. during a time period of 5 to 120 minutes. The pump is stopped after the time that is assumed to be optimal and the vessel containing the pancreas is carefully shaken for 3 to 20 minutes by hand. If needed, the prior addition of metal balls additionally facilitates the mechanical dissociation of the tissue and release of the islets from the surrounding exocrine tissue.

The digestion is stopped by addition of ice-cold HBSS/ 10% FCS (foetal calf serum) and the suspension is filtered through a sieve (mesh size 300 μm) in order to separate coarse particles. The islets present in the filtrate are centrifuged for 10 minutes at 100 g in 250 ml Nalgene round-bottom flasks. The supernatant is decanted and the pellet containing the islets is resuspended in 50 ml FCS.

The islets can be purified further by means of a density gradient made by hand. Firstly 7 ml islet suspension is added to 250 ml Nalgene round-bottom flasks. These are firstly overlayered with 93 ml of a Ficoll® solution (φ=1.077 g/cm³), and then with 50 ml medium (RPMI 1640). These gradients are centrifuged for 10 minutes at 100 g in a swing-out rotor. Fractions of 10 ml are collected, the size, purity and yield of the islets stained with dithiozone is determined microscopically in every fraction or with the aid of image analysis.

List of References

Amann et al., Gene 40 (1985) 183
Angleton, E. L. and Van Wart, H. E., Biochemistry 27 (1988) 7413–7418 and 7406–7412
Beck and Zink, Gene 16 (1981) 35–58 Bond, M. D. and Van Wart, H. E., Biochemistry 23 (1984) 3077–3085
Bond, M. D. and Van Wart, H. E., Biochemistry 23 (1984) 3085–3091
Brosius et al., J.Mol.Biol. 148 (1981) 107–127
Chang et al., Nature 198 (1977) 1056
Davies et al., Ann.Rev.Microbiol. 32 (1978) 469
EP-A 0 267 851
EP-A 0 495 398
French, M. F., et al., J.Protein Chemistry 11 (1992) 83–97
Ghrayeb et al., EMBO J. 3 (1984) 2437
Goeddel et al., Nuc. Acids Res. 8 (1980) 4057
Hefley et al., J.Bone Mineral Res. 2 (1987) 505–516
Holzinger et al., Immunol. Lett. 35 (1993) 109–118
Kingsman, S.M. et al., Tibtech 5 (1987) 53–57
Miller et al., Bio/Technology 7 (1989) 698
Nagai et al., Nature 309 (1984) 810
Oka et al, Proc.Natl.Acad.Sci. USA 82 (1985) 7212
Palva et al., Proc.Natl.Acad.Sci. USA 79 (1982) 5582
Phillips and Silhavy, Nature 344 (1990) 882–884
Powell et al., Appl.Environ.Microbiol. 54 (1988) 655
Quibel et al, Anal.Biochem. 154 (1986) 26–28
Ricordi et al, Diabetes 37 (1988) 413–420
Sambrook et al., "Expression of cloned genes in *E. coli*" in Molecular Cloning: A laboratory manual (1989) Cold Spring Harbor Laboratory Press, New York, USA
Shimatake et al., Nature 292 (1981) 128
Studier et al., J.Mol.Biol. 189 (1986) 113
Sutton et al., Transplantation 42 (1986) 689–691
U.S. Pat. No. 4,551,433
U.S. Pat. No. 4,689,406
U.S. Pat. No. 4,747,056
U.S. Pat. No. 5,177,011
U.S. Pat. No. 5,418,157
Van Wart, H. E., Biochemistry 24 (1985) 6520–6526
WO 91/11520
WO 91/14447
WO 94/00580
Wolters, Hormone and Metabolic Research 26 (1994) p.80
Yansura, Meth.Enzymol. 185 (1990) 161–166

What is claimed is:

1. A polypeptide comprising the amino acid sequence SEQ ID NO: 2.

2. The polypeptide of claim 1 wherein the polypeptide is N-terminally extended by one or more amino acids of the sequence SEQ ID NO: 3.

3. A polypeptide encoded by the sequence SEQ ID NO: 1, wherein said coding begins at nucleotide 1002, 1029, 1110, 1176 or 1254 of SEQ ID NO: 1.

4. A method useful for the isolation of cells from mammalian tissue and human tissue, said method comprising contacting the tissue with the polypeptide of claim 1.

5. A method useful for the isolation of cells from mammalian tissue and human tissue, said method comprising contacting the tissue with the polypeptide of claim 2.

6. A method useful for the isolation of cells from mammalian tissue and human tissue, said method comprising contacting the tissue with the polypeptide of claim 3.

* * * * *

SEQUENCE LISTING

<160> NUMBER OF SEQ ID NOS: 24

<210> SEQ ID NO 1
<211> LENGTH: 4358
<212> TYPE: DNA
<213> ORGANISM: Clostridium histolyticum
<220> FEATURE:
<221> NAME/KEY: CDS
<222> LOCATION: (1332)..(4358)

<400> SEQUENCE: 1

```
aagcttttat aattctcact atactctcta gatggtataa taagagccca aaatacgaag     60
aatataataa aatataattt aaaaaggatg atttcaatgc gaaaaagagt ttttttgaat    120 atattttta ttttatgttc ctcaattttt tttatgtcct gcacaggaaa atttcaggtt    180
atagatcggg gtgatggggg agatgaaatt tatttaaaca aacaagatgg tgtgagtttt    240
gagattccta aagtgtggga taaaaattat aagattatca cttctagaga taaaagatat    300
ggcaaaaagt taacttttaa aaaaaaggat aagaaatgca acgttatact tttagaaata    360
tggattttga atgaggaata ttggagtgaa tttaaagatg ttaggaagtt taaacttata    420
ggtaaaagcg aaaaaggcgt agtagtttat tcaagaggta aattagatag catattagaa    480
```

-continued

```
aataatggat tggacattat gcatcataaa gaagagaaaa agaaagatat agaaaaaatg      540
tacattaaag atgaagaaat tagcgataga atcaaaataa ttagaaatta ataaaaaaat      600
gaaaatagaa aaattcattt tactaaaaat ttatgtttac tttctataac aatctttgta      660
aactgtaaat actaatgtag tatttttag aaaataataa tctgttaaaa agtgtattta       720
ggaactaaaa atgaataaat ttataaaaac tatttacaat atctaaaata atgtatataa      780
tttttattaa atagattatt ttggtattaa gggggtggtt gaaagaataa acagaaaatt      840
gatataattc aataaataaa atctaaagag aaatatctaa gtaatacaca aatctaatat      900
taaaatcatt ttaatattaa gaatattttg ttaataggta aaggttaaaa ggcattctat      960
tattaaggtt aaaaggtatt aattattaag ggggattatc tatgaaaaaa aatattttaa     1020
agattcttat ggatagttat tctaaagaat ctaaaattca aactgtacgt agggttacga     1080
gtgtatcact tttagcggca tatcttacta tgaatacttc aagtttagtt ttagcaaaac     1140
caatagaaaa tactaatgat actagtataa aaaatgtgga gaaattaaga aatgctccaa     1200
atgaagagaa tagtaaaaag gtagaagata gtaaaaatga taggtagaa catgtgaaaa      1260 atatagaaga ggcaaaggtt gagcaagttg cacccgaagt aaaatctaaa tcaactttaa     1320
gaagtgcttc t ata gcg aat act aat tct gag aaa tat gat ttt gag tat     1370
             Ile Ala Asn Thr Asn Ser Glu Lys Tyr Asp Phe Glu Tyr
              1               5                  10 tta aat ggt ttg agc tat act gaa ctt aca aat tta att aaa aat ata      1418
Leu Asn Gly Leu Ser Tyr Thr Glu Leu Thr Asn Leu Ile Lys Asn Ile
     15                  20                  25 aag tgg aat caa att aat ggt tta ttt aat tat agt aca ggt tct caa      1466
Lys Trp Asn Gln Ile Asn Gly Leu Phe Asn Tyr Ser Thr Gly Ser Gln
 30                  35                  40                  45 aag ttc ttt gga gat aaa aat cgt gta caa gct ata att aat gct tta      1514
Lys Phe Phe Gly Asp Lys Asn Arg Val Gln Ala Ile Ile Asn Ala Leu
                 50                  55                  60 caa gaa agt gga aga act tac act gca aat gat atg aag ggt ata gaa      1562
Gln Glu Ser Gly Arg Thr Tyr Thr Ala Asn Asp Met Lys Gly Ile Glu
             65                  70                  75 act ttc act gag gtt tta aga gct ggt ttt tat tta ggg tac tat aat      1610
Thr Phe Thr Glu Val Leu Arg Ala Gly Phe Tyr Leu Gly Tyr Tyr Asn
         80                  85                  90 gat ggt tta tct tat tta aat gat aga aac ttc caa gat aaa tgt ata      1658
Asp Gly Leu Ser Tyr Leu Asn Asp Arg Asn Phe Gln Asp Lys Cys Ile
     95                 100                 105 cct gca atg att gca att caa aaa aat cct aac ttt aag cta gga act      1706
Pro Ala Met Ile Ala Ile Gln Lys Asn Pro Asn Phe Lys Leu Gly Thr
110                 115                 120                 125 gca gtt caa gat gaa gtt ata act tct tta gga aaa cta ata gga aat      1754
Ala Val Gln Asp Glu Val Ile Thr Ser Leu Gly Lys Leu Ile Gly Asn
                130                 135                 140 gct tct gct aat gct gaa gta gtt aat aat tgt gta cca gtt cta aaa      1802
Ala Ser Ala Asn Ala Glu Val Val Asn Asn Cys Val Pro Val Leu Lys
            145                 150                 155 caa ttt aga gaa aac tta aat caa tat gct cct gat tac gtt aaa gga      1850
Gln Phe Arg Glu Asn Leu Asn Gln Tyr Ala Pro Asp Tyr Val Lys Gly
        160                 165                 170 aca gct gta aat gaa tta att aaa ggt att gaa ttc gat ttt tct ggt      1898
Thr Ala Val Asn Glu Leu Ile Lys Gly Ile Glu Phe Asp Phe Ser Gly
    175                 180                 185 gct gca tat gaa aaa gat gtt aag aca atg cct tgg tat gga aaa att      1946
Ala Ala Tyr Glu Lys Asp Val Lys Thr Met Pro Trp Tyr Gly Lys Ile
```

-continued

```
           190                195                200                205
gat cca ttt ata aat gaa ctt aag gcc tta ggt cta tat gga aat ata    1994
Asp Pro Phe Ile Asn Glu Leu Lys Ala Leu Gly Leu Tyr Gly Asn Ile
            210                215                220 aca agt gca act gag tgg gca tct gat gtt gga ata tac tat tta agt    2042
Thr Ser Ala Thr Glu Trp Ala Ser Asp Val Gly Ile Tyr Tyr Leu Ser
        225                230                235 aaa ttc ggg ctt tac tca act aac cga aat gac ata gta cag tca ctt    2090
Lys Phe Gly Leu Tyr Ser Thr Asn Arg Asn Asp Ile Val Gln Ser Leu
        240                245                250 gaa aag gct gta gat atg tat aag tat ggt aaa ata gcc ttt gta gca    2138
Glu Lys Ala Val Asp Met Tyr Lys Tyr Gly Lys Ile Ala Phe Val Ala
        255                260                265 atg gag aga ata act tgg gat tat gat ggg att ggt tct aat ggt aaa    2186
Met Glu Arg Ile Thr Trp Asp Tyr Asp Gly Ile Gly Ser Asn Gly Lys
270                275                280                285 aag gtg gat cac gat aag ttc tta gat gat gct gaa aaa cat tat ctg    2234
Lys Val Asp His Asp Lys Phe Leu Asp Asp Ala Glu Lys His Tyr Leu
            290                295                300 cca aag aca tat act ttt gat aat gga acc ttt att ata aga gca ggg    2282
Pro Lys Thr Tyr Thr Phe Asp Asn Gly Thr Phe Ile Ile Arg Ala Gly
        305                310                315 gat aag gta tcc gaa gaa aaa ata aaa agg cta tat tgg gca tca aga    2330
Asp Lys Val Ser Glu Glu Lys Ile Lys Arg Leu Tyr Trp Ala Ser Arg
        320                325                330 gaa gtg aag tct caa ttc cat aga gta gtt ggc aat gat aaa gct tta    2378
Glu Val Lys Ser Gln Phe His Arg Val Val Gly Asn Asp Lys Ala Leu
        335                340                345 gag gtg gga aat gcc gat gat gtt tta act atg aaa ata ttt aat agc    2426
Glu Val Gly Asn Ala Asp Asp Val Leu Thr Met Lys Ile Phe Asn Ser
350                355                360                365 cca gaa gaa tat aaa ttt aat acc aat ata aat ggt gta agt act gat    2474
Pro Glu Glu Tyr Lys Phe Asn Thr Asn Ile Asn Gly Val Ser Thr Asp
            370                375                380 aat ggt ggt cta tat ata gaa cca aga ggg act ttc tac act tat gag    2522
Asn Gly Gly Leu Tyr Ile Glu Pro Arg Gly Thr Phe Tyr Thr Tyr Glu
            385                390                395 aga aca cct caa caa agt ata ttt agt ctt gaa gaa ttg ttt aga cat    2570
Arg Thr Pro Gln Gln Ser Ile Phe Ser Leu Glu Glu Leu Phe Arg His
        400                405                410 gaa tat act cac tat tta caa gcg aga tat ctt gta gat ggt tta tgg    2618
Glu Tyr Thr His Tyr Leu Gln Ala Arg Tyr Leu Val Asp Gly Leu Trp
        415                420                425 ggg caa ggt cca ttt tat gaa aaa aat aga tta act tgg ttt gat gaa    2666
Gly Gln Gly Pro Phe Tyr Glu Lys Asn Arg Leu Thr Trp Phe Asp Glu
430                435                440                445 ggt aca gct gaa ttc ttt gca gga tct acc cgt aca tct ggt gtt tta    2714
Gly Thr Ala Glu Phe Phe Ala Gly Ser Thr Arg Thr Ser Gly Val Leu
            450                455                460 cca aga aaa tca ata tta gga tat ttg gct aag gat aaa gta gat cat    2762
Pro Arg Lys Ser Ile Leu Gly Tyr Leu Ala Lys Asp Lys Val Asp His
            465                470                475 aga tac tca tta aag aag act ctt aat tca ggg tat gat gac agt gat    2810
Arg Tyr Ser Leu Lys Lys Thr Leu Asn Ser Gly Tyr Asp Asp Ser Asp
        480                485                490 tgg atg ttc tat aat tat gga ttt gca gtt gca cat tac cta tat gaa    2858
Trp Met Phe Tyr Asn Tyr Gly Phe Ala Val Ala His Tyr Leu Tyr Glu
        495                500                505 aaa gat atg cct aca ttt att aag atg aat aaa gct ata ttg aat aca    2906
```

```
                                                                -continued

Lys Asp Met Pro Thr Phe Ile Lys Met Asn Lys Ala Ile Leu Asn Thr
510             515                 520                 525 gat gtg aaa tct tat gat gaa ata ata aaa aaa tta agt gat gat gca    2954
Asp Val Lys Ser Tyr Asp Glu Ile Ile Lys Lys Leu Ser Asp Asp Ala
                530                 535                 540 aat aaa aat aca gaa tat caa aac cat att caa gag tta gta gat aaa    3002
Asn Lys Asn Thr Glu Tyr Gln Asn His Ile Gln Glu Leu Val Asp Lys
                545                 550                 555 tat caa gga gct gga cta cct cta gta tca gat gat tac tta aaa gat    3050
Tyr Gln Gly Ala Gly Leu Pro Leu Val Ser Asp Asp Tyr Leu Lys Asp
            560                 565                 570 cat gga tat aag aaa gca tct gaa gta tat tct gaa att tca aaa gct    3098
His Gly Tyr Lys Lys Ala Ser Glu Val Tyr Ser Glu Ile Ser Lys Ala
    575                 580                 585 gct tct ctt aca aac act agt gta aca gca gaa aaa tct caa tac ttt    3146
Ala Ser Leu Thr Asn Thr Ser Val Thr Ala Glu Lys Ser Gln Tyr Phe
590                 595                 600                 605 aac aca ttc act tta aga gga act tat aca ggt gaa act tct aaa ggt    3194
Asn Thr Phe Thr Leu Arg Gly Thr Tyr Thr Gly Glu Thr Ser Lys Gly
                610                 615                 620 gaa ttt aaa gat tgg gat gaa atg agt aaa aaa tta gat gga act ttg    3242
Glu Phe Lys Asp Trp Asp Glu Met Ser Lys Lys Leu Asp Gly Thr Leu
                625                 630                 635 gag tcc ctt gct aaa aat tct tgg agt gga tac aaa acc tta aca gca    3290
Glu Ser Leu Ala Lys Asn Ser Trp Ser Gly Tyr Lys Thr Leu Thr Ala
            640                 645                 650 tac ttt acg aat tat aga gtt aca agc gat aat aaa gtt caa tat gat    3338
Tyr Phe Thr Asn Tyr Arg Val Thr Ser Asp Asn Lys Val Gln Tyr Asp
    655                 660                 665 gta gtt ttc cat ggg gtt tta aca gat aat ggg gat att agt aac aat    3386
Val Val Phe His Gly Val Leu Thr Asp Asn Gly Asp Ile Ser Asn Asn
670                 675                 680                 685 aag gct cca ata gca aag gta act gga cca agc act ggt gct gta gga    3434
Lys Ala Pro Ile Ala Lys Val Thr Gly Pro Ser Thr Gly Ala Val Gly
                690                 695                 700 aga aat att gaa ttt agt gga aaa gat agt aaa gat gaa gat ggt aaa    3482
Arg Asn Ile Glu Phe Ser Gly Lys Asp Ser Lys Asp Glu Asp Gly Lys
                705                 710                 715 ata gta tca tat gat tgg gat ttt ggc gat ggt gca act agt aga ggc    3530
Ile Val Ser Tyr Asp Trp Asp Phe Gly Asp Gly Ala Thr Ser Arg Gly
            720                 725                 730 aaa aat tca gta cat gct tac aaa aaa gca gga aca tat aat gtt aca    3578
Lys Asn Ser Val His Ala Tyr Lys Lys Ala Gly Thr Tyr Asn Val Thr
    735                 740                 745 tta aaa gta act gac gat aag ggt gca aca gct aca gaa agc ttt act    3626
Leu Lys Val Thr Asp Asp Lys Gly Ala Thr Ala Thr Glu Ser Phe Thr
750                 755                 760                 765 ata gaa ata aag aac gaa gat aca aca aca cct ata act aaa gaa atg    3674
Ile Glu Ile Lys Asn Glu Asp Thr Thr Thr Pro Ile Thr Lys Glu Met
                770                 775                 780 gaa cct aat gat gat ata aaa gag gct aat ggt cca ata gtt gaa ggt    3722
Glu Pro Asn Asp Asp Ile Lys Glu Ala Asn Gly Pro Ile Val Glu Gly
                785                 790                 795 gtt act gta aaa ggt gat tta aat ggt tct gat gat gct gat acc ttc    3770
Val Thr Val Lys Gly Asp Leu Asn Gly Ser Asp Asp Ala Asp Thr Phe
            800                 805                 810 tat ttt gat gta aaa gaa gat ggt gat gtt aca att gaa ctt cct tat    3818
Tyr Phe Asp Val Lys Glu Asp Gly Asp Val Thr Ile Glu Leu Pro Tyr
    815                 820                 825
```

-continued

| | | |
|---|---|---|
| tca ggg tca tct aat ttc aca tgg tta gtt tat aaa gag gga gac gat<br>Ser Gly Ser Ser Asn Phe Thr Trp Leu Val Tyr Lys Glu Gly Asp Asp<br>830                   835                 840                 845 | | 3866 |
| caa aat cat att gca agt ggt ata gat aag aat aac tca aaa gtt gga<br>Gln Asn His Ile Ala Ser Gly Ile Asp Lys Asn Asn Ser Lys Val Gly<br>                 850                 855                 860 | | 3914 |
| aca ttt aaa gct aca aaa gga aga cat tat gtg ttt ata tat aaa cac<br>Thr Phe Lys Ala Thr Lys Gly Arg His Tyr Val Phe Ile Tyr Lys His<br>865                   870                 875 | | 3962 |
| gat tct gct tca aat ata tcc tat tct tta aac ata aaa gga tta ggt<br>Asp Ser Ala Ser Asn Ile Ser Tyr Ser Leu Asn Ile Lys Gly Leu Gly<br>                 880                 885                 890 | | 4010 |
| aac gag aaa ttg aag gaa aaa gaa aat aat gat tct tct gat aaa gct<br>Asn Glu Lys Leu Lys Glu Lys Glu Asn Asn Asp Ser Ser Asp Lys Ala<br>895                   900                 905 | | 4058 |
| aca gtt ata cca aat ttc aat acc act atg caa ggt tca ctt tta ggt<br>Thr Val Ile Pro Asn Phe Asn Thr Thr Met Gln Gly Ser Leu Leu Gly<br>910                   915                 920                 925 | | 4106 |
| gat gat tca aga gat tat tat tct ttt gag gtt aag gaa gaa ggc gaa<br>Asp Asp Ser Arg Asp Tyr Tyr Ser Phe Glu Val Lys Glu Glu Gly Glu<br>                 930                 935                 940 | | 4154 |
| gtt aat ata gaa cta gat aaa aag gat gaa ttt ggt gta aca tgg aca<br>Val Asn Ile Glu Leu Asp Lys Lys Asp Glu Phe Gly Val Thr Trp Thr<br>945                   950                 955 | | 4202 |
| cta cat cca gag tca aat att aat gac aga ata act tac gga caa gtt<br>Leu His Pro Glu Ser Asn Ile Asn Asp Arg Ile Thr Tyr Gly Gln Val<br>                 960                 965                 970 | | 4250 |
| gat ggt aat aag gta tct aat aaa gtt aaa tta aga cca gga aaa tat<br>Asp Gly Asn Lys Val Ser Asn Lys Val Lys Leu Arg Pro Gly Lys Tyr<br>975                   980                 985 | | 4298 |
| tat cta ctt gtt tat aaa tac tca gga tca gga aac tat gag tta agg<br>Tyr Leu Leu Val Tyr Lys Tyr Ser Gly Ser Gly Asn Tyr Glu Leu Arg<br>990                   995                 1000              1005 | | 4346 |
| gta aat aaa taa<br>Val Asn Lys | | 4358 |

<210> SEQ ID NO 2
<211> LENGTH: 1008
<212> TYPE: PRT
<213> ORGANISM: Clostridium histolyticum

<400> SEQUENCE: 2

Ile Ala Asn Thr Asn Ser Glu Lys Tyr Asp Phe Glu Tyr Leu Asn Gly
1               5                   10                  15

Leu Ser Tyr Thr Glu Leu Thr Asn Leu Ile Lys Asn Ile Lys Trp Asn
                20                  25                  30

Gln Ile Asn Gly Leu Phe Asn Tyr Ser Thr Gly Ser Gln Lys Phe Phe
            35                  40                  45

Gly Asp Lys Asn Arg Val Gln Ala Ile Ile Asn Ala Leu Gln Glu Ser
        50                  55                  60

Gly Arg Thr Tyr Thr Ala Asn Asp Met Lys Gly Ile Glu Thr Phe Thr
65                  70                  75                  80

Glu Val Leu Arg Ala Gly Phe Tyr Leu Gly Tyr Tyr Asn Asp Gly Leu
                85                  90                  95

Ser Tyr Leu Asn Asp Arg Asn Phe Gln Asp Lys Cys Ile Pro Ala Met
            100                 105                 110

Ile Ala Ile Gln Lys Asn Pro Asn Phe Lys Leu Gly Thr Ala Val Gln
        115                 120                 125

```
Asp Glu Val Ile Thr Ser Leu Gly Lys Leu Ile Gly Asn Ala Ser Ala
    130                 135                 140

Asn Ala Glu Val Val Asn Asn Cys Val Pro Val Leu Lys Gln Phe Arg
145                 150                 155                 160

Glu Asn Leu Asn Gln Tyr Ala Pro Asp Tyr Val Lys Gly Thr Ala Val
                165                 170                 175

Asn Glu Leu Ile Lys Gly Ile Glu Phe Asp Phe Ser Gly Ala Ala Tyr
            180                 185                 190

Glu Lys Asp Val Lys Thr Met Pro Trp Tyr Gly Lys Ile Asp Pro Phe
        195                 200                 205

Ile Asn Glu Leu Lys Ala Leu Gly Leu Tyr Gly Asn Ile Thr Ser Ala
    210                 215                 220

Thr Glu Trp Ala Ser Asp Val Gly Ile Tyr Leu Ser Lys Phe Gly
225                 230                 235                 240

Leu Tyr Ser Thr Asn Arg Asn Asp Ile Val Gln Ser Leu Glu Lys Ala
                245                 250                 255

Val Asp Met Tyr Lys Tyr Gly Lys Ile Ala Phe Val Ala Met Glu Arg
            260                 265                 270

Ile Thr Trp Asp Tyr Asp Gly Ile Gly Ser Asn Gly Lys Lys Val Asp
        275                 280                 285

His Asp Lys Phe Leu Asp Ala Glu Lys His Tyr Leu Pro Lys Thr
    290                 295                 300

Tyr Thr Phe Asp Asn Gly Thr Phe Ile Ile Arg Ala Gly Asp Lys Val
305                 310                 315                 320

Ser Glu Glu Lys Ile Lys Arg Leu Tyr Trp Ala Ser Arg Glu Val Lys
                325                 330                 335

Ser Gln Phe His Arg Val Val Gly Asn Asp Lys Ala Leu Glu Val Gly
            340                 345                 350

Asn Ala Asp Asp Val Leu Thr Met Lys Ile Phe Asn Ser Pro Glu Glu
        355                 360                 365

Tyr Lys Phe Asn Thr Asn Ile Asn Gly Val Ser Thr Asp Asn Gly Gly
    370                 375                 380

Leu Tyr Ile Glu Pro Arg Gly Thr Phe Tyr Thr Tyr Glu Arg Thr Pro
385                 390                 395                 400

Gln Gln Ser Ile Phe Ser Leu Glu Glu Leu Phe Arg His Glu Tyr Thr
                405                 410                 415

His Tyr Leu Gln Ala Arg Tyr Leu Val Asp Gly Leu Trp Gly Gln Gly
            420                 425                 430

Pro Phe Tyr Glu Lys Asn Arg Leu Thr Trp Phe Asp Glu Gly Thr Ala
        435                 440                 445

Glu Phe Phe Ala Gly Ser Thr Arg Thr Ser Gly Val Leu Pro Arg Lys
450                 455                 460

Ser Ile Leu Gly Tyr Leu Ala Lys Asp Lys Val Asp His Arg Tyr Ser
465                 470                 475                 480

Leu Lys Lys Thr Leu Asn Ser Gly Tyr Asp Asp Ser Asp Trp Met Phe
                485                 490                 495

Tyr Asn Tyr Gly Phe Ala Val Ala His Tyr Leu Tyr Glu Lys Asp Met
            500                 505                 510

Pro Thr Phe Ile Lys Met Asn Lys Ala Ile Leu Asn Thr Asp Val Lys
        515                 520                 525

Ser Tyr Asp Glu Ile Ile Lys Lys Leu Ser Asp Ala Asn Lys Asn
    530                 535                 540

Thr Glu Tyr Gln Asn His Ile Gln Glu Leu Val Asp Lys Tyr Gln Gly
```

-continued

```
545                 550                 555                 560
Ala Gly Leu Pro Leu Val Ser Asp Asp Tyr Leu Lys Asp His Gly Tyr
                565                 570                 575

Lys Lys Ala Ser Glu Val Tyr Ser Glu Ile Ser Lys Ala Ala Ser Leu
                580                 585                 590

Thr Asn Thr Ser Val Thr Ala Glu Lys Ser Gln Tyr Phe Asn Thr Phe
                595                 600                 605

Thr Leu Arg Gly Thr Tyr Thr Gly Glu Thr Ser Lys Gly Glu Phe Lys
            610                 615                 620

Asp Trp Asp Glu Met Ser Lys Lys Leu Asp Gly Thr Leu Glu Ser Leu
625                 630                 635                 640

Ala Lys Asn Ser Trp Ser Gly Tyr Lys Thr Leu Thr Ala Tyr Phe Thr
                645                 650                 655

Asn Tyr Arg Val Thr Ser Asp Asn Lys Val Gln Tyr Asp Val Val Phe
                660                 665                 670

His Gly Val Leu Thr Asp Asn Gly Asp Ile Ser Asn Asn Lys Ala Pro
            675                 680                 685

Ile Ala Lys Val Thr Gly Pro Ser Thr Gly Ala Val Gly Arg Asn Ile
        690                 695                 700

Glu Phe Ser Gly Lys Asp Ser Lys Asp Glu Asp Gly Lys Ile Val Ser
705                 710                 715                 720

Tyr Asp Trp Asp Phe Gly Asp Gly Ala Thr Ser Arg Gly Lys Asn Ser
                725                 730                 735

Val His Ala Tyr Lys Lys Ala Gly Thr Tyr Asn Val Thr Leu Lys Val
            740                 745                 750

Thr Asp Asp Lys Gly Ala Thr Ala Thr Glu Ser Phe Thr Ile Glu Ile
        755                 760                 765

Lys Asn Glu Asp Thr Thr Thr Pro Ile Thr Lys Glu Met Glu Pro Asn
    770                 775                 780

Asp Asp Ile Lys Glu Ala Asn Gly Pro Ile Val Glu Gly Val Thr Val
785                 790                 795                 800

Lys Gly Asp Leu Asn Gly Ser Asp Asp Ala Asp Thr Phe Tyr Phe Asp
                805                 810                 815

Val Lys Glu Asp Gly Asp Val Thr Ile Glu Leu Pro Tyr Ser Gly Ser
            820                 825                 830

Ser Asn Phe Thr Trp Leu Val Tyr Lys Glu Gly Asp Asp Gln Asn His
            835                 840                 845

Ile Ala Ser Gly Ile Asp Lys Asn Asn Ser Lys Val Gly Thr Phe Lys
    850                 855                 860

Ala Thr Lys Gly Arg His Tyr Val Phe Ile Tyr Lys His Asp Ser Ala
865                 870                 875                 880

Ser Asn Ile Ser Tyr Ser Leu Asn Ile Lys Gly Leu Gly Asn Glu Lys
                885                 890                 895

Leu Lys Glu Lys Glu Asn Asn Asp Ser Ser Asp Lys Ala Thr Val Ile
            900                 905                 910

Pro Asn Phe Asn Thr Thr Met Gln Gly Ser Leu Leu Gly Asp Asp Ser
        915                 920                 925

Arg Asp Tyr Tyr Ser Phe Glu Val Lys Glu Gly Glu Val Asn Ile
    930                 935                 940

Glu Leu Asp Lys Lys Asp Glu Phe Gly Val Thr Trp Thr Leu His Pro
945                 950                 955                 960

Glu Ser Asn Ile Asn Asp Arg Ile Thr Tyr Gly Gln Val Asp Gly Asn
                965                 970                 975
```

```
Lys Val Ser Asn Lys Val Lys Leu Arg Pro Gly Lys Tyr Tyr Leu Leu
            980                 985                 990

Val Tyr Lys Tyr Ser Gly Ser Gly  Asn Tyr Glu Leu Arg  Val Asn Lys
            995             1000                 1005

<210> SEQ ID NO 3
<211> LENGTH: 110
<212> TYPE: PRT
<213> ORGANISM: Clostridium histolyticum

<400> SEQUENCE: 3

Met Lys Lys Asn Ile Leu Lys Ile Leu Met Asp Ser Tyr Ser Lys Glu
1               5                   10                  15

Ser Lys Ile Gln Thr Val Arg Arg Val Thr Ser Val Ser Leu Leu Ala
            20                  25                  30

Ala Tyr Leu Thr Met Asn Thr Ser Ser Leu Val Leu Ala Lys Pro Ile
            35                  40                  45

Glu Asn Thr Asn Asp Thr Ser Ile Lys Asn Val Glu Lys Leu Arg Asn
    50                  55                  60

Ala Pro Asn Glu Glu Asn Ser Lys Lys Val Glu Asp Ser Lys Asn Asp
65                  70                  75                  80

Lys Val Glu His Val Lys Asn Ile Glu Glu Ala Lys Val Glu Gln Val
                85                  90                  95

Ala Pro Glu Val Lys Ser Lys Ser Thr Leu Arg Ser Ala Ser
            100                 105                 110

<210> SEQ ID NO 4
<211> LENGTH: 7
<212> TYPE: PRT
<213> ORGANISM: Clostridium histolyticum

<400> SEQUENCE: 4

Phe Asn Ser Pro Glu Glu Tyr
1               5

<210> SEQ ID NO 5
<211> LENGTH: 7
<212> TYPE: PRT
<213> ORGANISM: Clostridium histolyticum

<400> SEQUENCE: 5

Glu Asp Gly Asp Val Thr Ile
1               5

<210> SEQ ID NO 6
<211> LENGTH: 21
<212> TYPE: DNA
<213> ORGANISM: Artificial sequence
<220> FEATURE:
<221> NAME/KEY: misc_feature
<222> LOCATION: (9)..(9)
<223> OTHER INFORMATION: can be any nucleotide
<221> NAME/KEY: misc_feature
<222> LOCATION: (12)..(12)
<223> OTHER INFORMATION: can be any nucleotide

<400> SEQUENCE: 6
ttyaaywsnc cngargarta y                                       21

<210> SEQ ID NO 7
<211> LENGTH: 21
<212> TYPE: DNA
```

```
<213> ORGANISM: Artificial sequence
<220> FEATURE:
<221> NAME/KEY: misc_feature
<222> LOCATION: (10)..(10)
<223> OTHER INFORMATION: can be any nucleotide
<221> NAME/KEY: misc_feature
<222> LOCATION: (13)..(13)
<223> OTHER INFORMATION: can be any nucleotide

<400> SEQUENCE: 7
rtaytcytcn ggnswrttra a                                              21

<210> SEQ ID NO 8
<211> LENGTH: 21
<212> TYPE: DNA
<213> ORGANISM: Artificial sequence
<220> FEATURE:
<221> NAME/KEY: misc_feature
<222> LOCATION: (9)..(9)
<223> OTHER INFORMATION: can be any nucleotide
<221> NAME/KEY: misc_feature
<222> LOCATION: (15)..(15)
<223> OTHER INFORMATION: can be any nucleotide
<221> NAME/KEY: misc_feature
<222> LOCATION: (18)..(18)
<223> OTHER INFORMATION: can be any nucleotide

<400> SEQUENCE: 8
gargayggng aygtnacnat t                                              21

<210> SEQ ID NO 9
<211> LENGTH: 21
<212> TYPE: DNA
<213> ORGANISM: Artificial sequence
<220> FEATURE:
<221> NAME/KEY: misc_feature
<222> LOCATION: (4)..(4)
<223> OTHER INFORMATION: can be any nucleotide
<221> NAME/KEY: misc_feature
<222> LOCATION: (7)..(7)
<223> OTHER INFORMATION: can be any nucleotide
<221> NAME/KEY: misc_feature
<222> LOCATION: (13)..(13)
<223> OTHER INFORMATION: can be any nucleotide

<400> SEQUENCE: 9
datngtnacr tnccrtcyt c                                               21

<210> SEQ ID NO 10
<211> LENGTH: 7
<212> TYPE: PRT
<213> ORGANISM: Clostridium histolyticum

<400> SEQUENCE: 10

Asp Trp Asp Glu Met Ser Lys
1               5

<210> SEQ ID NO 11
<211> LENGTH: 18
<212> TYPE: PRT
<213> ORGANISM: Clostridium histolyticum

<400> SEQUENCE: 11

Val Thr Gly Pro Ser Thr Gly Ala Val Gly Arg Asn Ile Glu Phe Ser
1               5                   10                  15
Gly Lys

<210> SEQ ID NO 12
```

-continued

```
<211> LENGTH: 14
<212> TYPE: PRT
<213> ORGANISM: Clostridium histolyticum

<400> SEQUENCE: 12

Asn Thr Glu Tyr Gln Asn His Ile Gln Glu Leu Val Asp Lys
1               5                   10

<210> SEQ ID NO 13
<211> LENGTH: 22
<212> TYPE: PRT
<213> ORGANISM: Clostridium histolyticum

<400> SEQUENCE: 13

Glu Asp Gly Asp Val Thr Ile Glu Leu Pro Tyr Ser Gly Ser Ser Asn
1               5                   10                  15

Phe Thr Trp Leu Val Tyr
            20

<210> SEQ ID NO 14
<211> LENGTH: 15
<212> TYPE: PRT
<213> ORGANISM: Clostridium histolyticum

<400> SEQUENCE: 14

Gln Phe Arg Glu Asn Leu Asn Gln Tyr Ala Pro Asp Tyr Val Lys
1               5                   10                  15

<210> SEQ ID NO 15
<211> LENGTH: 19
<212> TYPE: DNA
<213> ORGANISM: Clostridium histolyticum

<400> SEQUENCE: 15
agacaatgcc ttggtatgg                                            19

<210> SEQ ID NO 16
<211> LENGTH: 21
<212> TYPE: DNA
<213> ORGANISM: Clostridium histolyticum

<400> SEQUENCE: 16
gtgaaagttt ctataccctt c                                         21

<210> SEQ ID NO 17
<211> LENGTH: 20
<212> TYPE: DNA
<213> ORGANISM: Clostridium histolyticum

<400> SEQUENCE: 17
gtacaggttc tcaaaagttc                                           20

<210> SEQ ID NO 18
<211> LENGTH: 20
<212> TYPE: DNA
<213> ORGANISM: Clostridium histolyticum

<400> SEQUENCE: 18
gttcctttaa cgtaatcagg                                           20

<210> SEQ ID NO 19
<211> LENGTH: 8
<212> TYPE: PRT
<213> ORGANISM: Clostridium histolyticum
```

```
<400> SEQUENCE: 19

Ile Ala Asn Thr Asn Ser Glu Lys
1               5

<210> SEQ ID NO 20
<211> LENGTH: 18
<212> TYPE: PRT
<213> ORGANISM: Clostridium histolyticum

<400> SEQUENCE: 20

Met Thr Met Ile Thr Asn Ser Arg Ala Met Lys Lys Asn Ile Leu Lys
1               5                   10                  15

Ile Leu

<210> SEQ ID NO 21
<211> LENGTH: 18
<212> TYPE: PRT
<213> ORGANISM: Clostridium histolyticum

<400> SEQUENCE: 21

Met Thr Met Ile Thr Asn Ser Arg Ala Met Asp Ser Tyr Ser Lys Glu
1               5                   10                  15

Ser Lys

<210> SEQ ID NO 22
<211> LENGTH: 18
<212> TYPE: PRT
<213> ORGANISM: Clostridium histolyticum

<400> SEQUENCE: 22

Met Thr Met Ile Thr Asn Ser Arg Ala Met Lys Asn Ile Glu Glu Ala
1               5                   10                  15

Lys Val

<210> SEQ ID NO 23
<211> LENGTH: 42
<212> TYPE: DNA
<213> ORGANISM: Clostridium histolyticum

<400> SEQUENCE: 23
ttcccaattg cccgggctat gaaaaatata gaagaggcaa ag          42

<210> SEQ ID NO 24
<211> LENGTH: 8
<212> TYPE: PRT
<213> ORGANISM: Clostridium histolyticum

<400> SEQUENCE: 24

Ala Tyr Leu Thr Met Asn Thr Ser
1               5
```